(12) United States Patent
Adachi et al.

(10) Patent No.: US 9,645,160 B2
(45) Date of Patent: May 9, 2017

(54) AUTOMATIC ANALYSIS DEVICE

(75) Inventors: Sakuichiro Adachi, Tokyo (JP);
Tomonori Mimura, Tokyo (JP);
Hajime Yamazaki, Tokyo (JP); Masaki Shiba, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 302 days.

(21) Appl. No.: 14/116,177

(22) PCT Filed: May 9, 2012

(86) PCT No.: PCT/JP2012/003018
§ 371 (c)(1),
(2), (4) Date: Jan. 31, 2014

(87) PCT Pub. No.: WO2012/157206
PCT Pub. Date: Nov. 22, 2012

(65) Prior Publication Data
US 2014/0140890 A1  May 22, 2014

(30) Foreign Application Priority Data

May 13, 2011 (JP) ................. 2011-107837

(51) Int. Cl.
*G01N 35/02* (2006.01)
*G01N 21/51* (2006.01)
(Continued)

(52) U.S. Cl.
CPC ........... *G01N 35/025* (2013.01); *G01N 21/51* (2013.01); *G01N 21/82* (2013.01); *G01N 2021/4711* (2013.01); *G01N 2035/0453* (2013.01)

(58) Field of Classification Search
None
See application file for complete search history.

(56) References Cited

U.S. PATENT DOCUMENTS 4,401,387 A  8/1983 Tokinage et al.
4,451,433 A  5/1984 Yamashita et al.
(Continued)

FOREIGN PATENT DOCUMENTS

DE  WO 2011104039 A1 * 9/2011 ........... G01N 21/274
EP  1464966 A1 * 10/2004
(Continued)

OTHER PUBLICATIONS

European Search Report received in corresponding European Application No. 12784970 dated Sep. 10, 2014.
(Continued)

*Primary Examiner* — Sally Merkling
*Assistant Examiner* — Benjamin Whatley
(74) *Attorney, Agent, or Firm* — Mattingly & Malur, PC

(57) ABSTRACT

The automatic analysis device measures time sequential data on a scattered light amount as reaction process data, and quantitatively determines the concentration of an analyte from a change in light amount. The automatic analysis device has a function of selecting reaction process data to be used for quantitative determination from the reaction process data obtained by measurement using a plurality of light receivers at different angles. As a result of using this function, data is selected from the reaction process data obtained by measurement using the plurality of light receivers at different angles in accordance with the concentration of the analyte and whether the priority is given to high sensitivity in the case where sensitivity is prioritized or a dynamic range, and the result of the quantitative determination is displayed.

8 Claims, 12 Drawing Sheets

(51) Int. Cl.
*G01N 21/82* (2006.01)
*G01N 21/47* (2006.01)
*G01N 35/04* (2006.01)

(56) References Cited

U.S. PATENT DOCUMENTS

| | | | |
|---|---|---|---|
| 4,766,083 A | 8/1988 | Miyashita et al. | |
| 6,791,676 B1 | 9/2004 | Meller | |
| 2004/0036874 A1* | 2/2004 | Kramer | G01N 15/1459 356/342 |
| 2006/0038994 A1* | 2/2006 | Chrisp | G01J 3/2823 356/328 |
| 2008/0020481 A1* | 1/2008 | Yamamoto | G01N 35/025 436/164 |
| 2008/0108103 A1* | 5/2008 | Ishisaka | G01N 15/1459 435/29 |
| 2008/0218751 A1* | 9/2008 | Togashi | G01N 21/9503 356/237.5 |
| 2009/0075248 A1* | 3/2009 | Debreczeny | G01N 15/06 435/3 |
| 2009/0122313 A1* | 5/2009 | Jones | G01N 15/0205 356/326 |
| 2009/0324036 A1* | 12/2009 | Batistoni | G01N 21/82 382/128 |
| 2011/0043807 A1* | 2/2011 | Andelic | G01N 21/49 356/441 |
| 2011/0060533 A1* | 3/2011 | Jorden | G01N 33/18 702/23 |
| 2011/0104743 A1* | 5/2011 | Maurer | G01N 15/05 435/34 |
| 2011/0223066 A1* | 9/2011 | Yamazaki | G01N 21/274 422/82.09 |
| 2012/0120385 A1* | 5/2012 | Jiang | C12Q 1/04 356/51 |
| 2012/0130649 A1* | 5/2012 | Salerno | G01N 21/0303 702/23 |
| 2012/0141330 A1* | 6/2012 | Adachi | G01N 21/51 422/82.05 |
| 2012/0274760 A1* | 11/2012 | King | G01N 15/1463 348/135 |
| 2012/0287435 A1* | 11/2012 | Adams | G01N 21/51 356/340 |
| 2012/0293796 A1* | 11/2012 | Ludowise | B01L 3/5027 356/244 |
| 2013/0108509 A1* | 5/2013 | Shiba | G01N 21/51 422/82.05 |
| 2015/0355182 A1* | 12/2015 | Rissin | G01N 21/6452 506/9 |

FOREIGN PATENT DOCUMENTS

| | | | |
|---|---|---|---|
| JP | 58-172537 A | | 10/1983 |
| JP | 3059123 U | * | 7/1999 |
| JP | 2001-141654 A | | 5/2001 |
| JP | 2008064594 A | * | 3/2008 |
| JP | 2009281930 A | * | 12/2009 |
| WO | 2011/004781 A1 | | 1/2011 |
| WO | 2011/068049 A1 | | 6/2011 |
| WO | 2011/162113 A1 | | 12/2011 |

OTHER PUBLICATIONS

J. Sarobe et al: "Nephelometric Assay of Immunoglobulin G Chemically Bound to Chloromethyl Styrene Beads", Polymers for Advanced Technologies, Wiley & Sons, Bognor Regis, GB, vol. 7, No. 9, Sep. 1, 1996, pp. 749-753.

J. Ortega-Vinuesa et al: "A comparative study of optical techniques applied to particle-enhanced assays of C-reactive protein—3. Association of latex particles modified with antigens and antibodies." Journal of Immunological Methods, Elsevier Science Publishes B.V., Amsterdam, NL, vol. 205, No. 2, Jul. 14, 1997, pp. 151-156.

* cited by examiner

FIG. 7

SAMPLE NUMBER | 1001 |    SAMPLE POSITION | 1 |

TEST ITEM NAME | CRP |

QUANTITATIVE DETERMINATION METHOD

| CHOICE | PRIORITY | REACTION PROCESS TYPE |
|--------|----------|----------------------|
| ☑ | HIGH SENSITIVITY | 30° |
| ☐ | DYNAMIC RANGE | 20° |

FIG. 9

| | | SAMPLE NUMBER | 1001 | | SAMPLE POSITION | 1 |

TEST ITEM  CRP

QUANTITATIVE DETERMINATION METHOD

| TYPE | REACTION PROCESS TYPE | LOWER THRESHOLD LIMIT (A.U.) | UPPER THRESHOLD LIMIT (A.U) |
|---|---|---|---|
| FIRST PRIORITY | 30° | 0 | 1.0 |
| SECOND PRIORITY | 20° | 0.8 | 10.0 |

FIG. 12

| | SAMPLE NUMBER | 1001 | SAMPLE POSITION | 1 |

TEST ITEM  CRP

QUANTITATIVE DETERMINATION METHOD

| TYPE | REACTION PROCESS TYPE | LOWER THRESHOLD LIMIT (mg/dL) | UPPER THRESHOLD LIMIT (mg/dL) |
|---|---|---|---|
| FIRST PRIORITY | 30° | 0 | 3.0 |
| SECOND PRIORITY | 20° | 2.0 | 100.0 |

| QUANTITATIVE ALARM VALUE | 0.1 mg/dL |

FIG. 13

SAMPLE NUMBER  1001    SAMPLE POSITION  1

QUANTITATIVE DETERMINATION RESULT

| TEST ITEM | QUANTITATIVE DETERMINATION RESULT | (ALARM) |
|---|---|---|
| CRP | 0.5 mg/dL (30°) | ! |

| DETAILED RESULTS | REACTION PROCESS TYPE | QUANTITATIVE DETERMINATION RESULT (mg/dL) |
|---|---|---|
| | 30° | 0.5 mg/dL |
| | 20° | 0.8 mg/dL |

AUTOMATIC ANALYSIS DEVICE

TECHNICAL FIELD

The present invention relates to an analysis device, which measures the concentration of an analyte contained in a sample, for example, an automatic analysis device, which quantitatively determines the concentration of an analyte contained in blood or urine.

BACKGROUND ART

An automatic analysis device, which irradiates a reaction mixture obtained by mixing a sample with a reagent with a light from a light source, calculates an absorbance from a change in the amount of a transmitted light with a specific wavelength, and quantitatively determines the concentration of an analyte according to the Lambert-Beer law, has been widely used (for example, PTL 1). In such a device, in a cell disk which repeats rotation and stop, a lot of cells each retaining a reaction mixture are arranged on a circumference thereof, time sequential data on the amount of a transmitted light transmitted through the reaction mixture in the cell is measured as reaction process data at about 15 second intervals for about 10 minutes by a transmitted light measuring section disposed at a given position during the rotation of the cell disk, an absorbance is calculated from a change in light amount, and the concentration of an analyte is quantitatively determined.

As the reaction for which the measurement is performed by the automatic analysis device, there are mainly the following two types of reactions: a color reaction in which a substrate and an enzyme are reacted with each other, and an immune agglutination reaction in which an antigen and an antibody are reacted with each other. An analysis using the former reaction is called a biochemical analysis, and examples of a test item include LDH (lactate dehydrogenase), ALP (alkaline phosphatase), and AST (aspartate-oxoglutarate aminotransferase). An analysis using the latter reaction is called an immunoassay, and examples of a test item include CRP (C-reactive protein), IgG (immunoglobulin), and RF (rheumatoid factor). In an analyte to be measured in the latter reaction, there is a test item requiring quantitative determination in a low concentration range in which the blood concentration is low, and for such a test item, a latex immunoassay in which latex particles having a surface sensitized (bound) with an antibody are used as a sensitizer is used. In the latex immunoassay, an agglutinated body produced by agglutinating the latex particles by an analyte is irradiated with a light, and the amount of a transmitted light transmitted without scattering is measured. The size of the agglutinated body after the lapse of a predetermined time is increased as the concentration of an analyte is increased, and therefore, the concentration of the analyte can be quantitatively determined from a light amount measured as reaction process data.

Recently, it has been demanded that a latex immunoassay have higher sensitivity. A large number of reagents for use in an automatic analysis device have been developed so far, however, there are the following two types of reagents: a reagent for use in a normal analysis and a reagent compatible with a highly sensitive analysis, and a user needs to select a reagent depending on the intended use. Further, as for the device, in order to further increase the sensitivity of the latex immunoassay, it has been tried to measure a scattered light not to measure a transmitted light so far. For example, a system which separates a transmitted light and a scattered light from each other using a diaphragm and simultaneously measures an absorbance and a scattered light (PTL 2), etc. have been disclosed.

CITATION LIST

Patent Literature

PTL 1: U.S. Pat. No. 4,451,433
PTL 2: JP-A-2001-141654

SUMMARY OF INVENTION

Technical Problem

The measurement of a scattered light enables detection of a change in light amount largely even in a low concentration range as compared with the measurement of a transmitted light, but has a problem that it is susceptible to noise from dust or an air bubble due to the low light amount as compared with a transmitted light. In particular, in the automatic analysis device, a constant temperature fluid is circulated around a cell for stabilizing the temperature of the reaction mixture, and therefore, dust or an air bubble is likely to be present. There was no structure capable of performing measurement with high sensitivity even under such a circumstance.

Even if measurement with high sensitivity can be performed, the measurement of a scattered light has a problem that a change in light amount is small in a high concentration range and a dynamic range (a quantitatively determinable range) is decreased. For example, PTL 2 discloses a structure enabling the measurement in a low concentration range, however, a technique for expanding a dynamic range has not been disclosed yet.

As a result, in the measurement of a scattered light, a structure in which an effect of dust or an air bubble is small and a dynamic range is expanded has not been disclosed. A user needs to change a reagent or a device when a normal test in which a dynamic range is wide and a highly sensitive test in which quantitative determination performance in a low concentration range is high are performed even if the test item is the same, and there has been no technique in which such tests are achieved by one measurement using the same device and the same reagent.

Solution to Problem

The present invention provides an automatic analysis device which measures time sequential data on a scattered light amount as reaction process data, and quantitatively determines the concentration of an analyte from a change in light amount. The automatic analysis device has a function of selecting reaction process data to be used for quantitative determination from the reaction process data obtained by measurement using a plurality of light receivers at different angles. As a result of using this function, data is selected from the reaction process data obtained by measurement using the plurality of light receivers at different angles in accordance with the concentration of the analyte and whether the priority is given to high sensitivity in the case where sensitivity is prioritized or a dynamic range, and the result of the quantitative determination is displayed.

That is, a representative configuration of the automatic analysis device of the present invention includes: a cell in which a reaction mixture obtained by mixing a sample with a reagent is placed; a cell disk which holds the cell on a circumference thereof and repeats rotation and stop; a light source which irradiates the cell with a light; a plurality of light receivers which receive a scattered light due to the reaction mixture placed in the cell at different light-receiving angles, respectively; a data processing section which processes reaction process data on the reaction mixture obtained by measurement using the plurality of light receivers; and an output section which outputs the result of processing by the data processing section, wherein the data processing section has information on the light-receiving angles of the plurality of light receivers, selects reaction process data to be used for outputting a quantitative value of the reaction mixture from the reaction process data obtained by measurement using the plurality of light receivers on the basis of the information on the light-receiving angles of the plurality of light receivers, and outputs the quantitative value of the reaction mixture obtained by calculation from the selected reaction process data.

Advantageous Effects of Invention

According to the present invention, it becomes possible to perform quantitative determination suitable for both of a highly sensitive test and a test in which the priority is given to a dynamic range without altering a device or a reagent.

BRIEF DESCRIPTION OF DRAWINGS

FIG. 7 shows an example of a setting screen.

FIG. 9 shows an example of a setting screen.

FIG. 12 shows an example of a setting screen.

FIG. 13 shows an example of a display of a quantitative determination result.

DESCRIPTION OF EMBODIMENTS

Hereinafter, embodiments of the present invention will be described with reference to the drawings.

First Embodiment

A case where light receivers are disposed at positions of 20° and 30° with respect to a light emitted from a light source as a plurality of light-receiving angles at which a scattered light is measured, a user designates whether the priority is given to a dynamic range or high sensitivity, and a quantitative determination result on the basis of reaction process data obtained by measurement at a light-receiving angle in accordance with the designation is displayed will be described.

Figure 5:
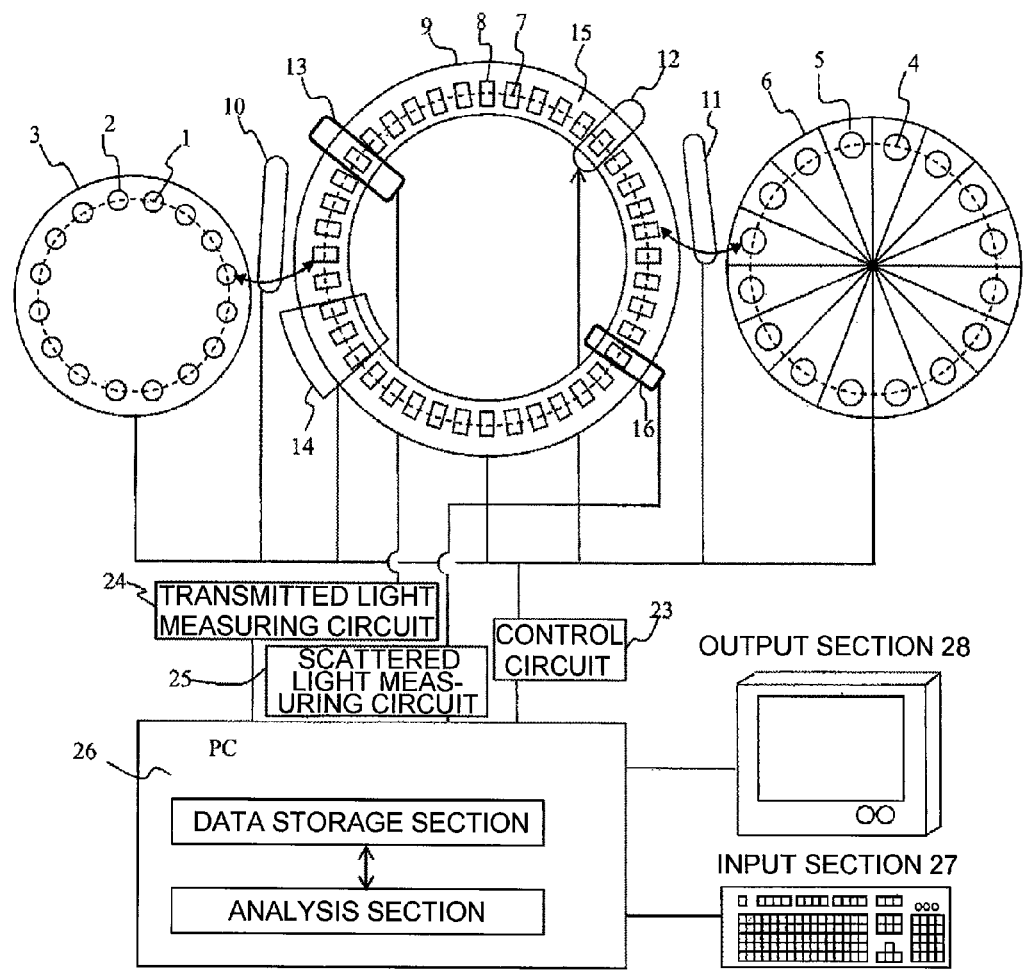
FIG. 5 is a schematic view showing an overall structural example of an automatic analysis device.

FIG. 5 is a schematic view showing an overall structural example of an automatic analysis device according to the present invention. This automatic analysis device is mounted with a scattered light measuring circuit. The automatic analysis device mainly includes the following three types of disks: a sample disk 3, a reagent disk 6, and a cell disk 9, dispensing mechanisms which transfer a sample or a reagent between these disks, a control circuit 23 which controls these members, a transmitted light measuring circuit 24, a scattered light measuring circuit 25, an analysis section in a data processing section 26 such as a PC (computer) which processes data obtained by measurement, a data storage section which stores control data, measurement data, data to be used for an analysis, and analysis result data, and an input section 27 and an output section 28 serving as an interface which inputs or outputs data with respect to the data storage section.

In the sample disk 3, a plurality of sample cups 2 in which a sample 1 is placed are arranged on a circumference thereof. In the sample disk 6, a plurality of reagent bottles 5 in which a reagent 4 is placed are arranged. In the cell disk 9, a plurality of cells 8 in which the sample 1 and the reagent 4 are mixed to form a reaction mixture 7 are arranged on a circumference thereof. A sample dispensing mechanism 10 transfers a given amount of the sample 1 from the sample cup 2 to the cell 8. A reagent dispensing mechanism 11 transfers a given amount of the reagent 4 from the reagent bottle 5 to the cell 8. A stirring section 12 stirs and mixes the sample 1 and the reagent 4 in the cell 8. A washing section 14 discharges the reaction mixture 7 from the cell 8 after completion of the analysis and washes the cell 8. To the washed cell 8, a subsequent sample 1 is dispensed again by the sample dispensing mechanism 10, and a fresh reagent 4 is dispensed by the reagent dispensing mechanism 11, and thus, the cell 8 is used for another reaction. The cell 8 is immersed in a constant temperature fluid 15 in a constant temperature bath in which the temperature and the flow rate are controlled, and is moved in a state where the temperatures of the cell 8 and the reaction mixture 7 therein are maintained constant. As the constant temperature fluid 15, water is used, and the temperature of the constant temperature fluid is regulated at 37±0.1° C. by the control circuit. A transmitted light measuring section 13 and a scattered light measuring section 16 are fitted to a part of the cell disk on a circumference thereof.

The transmitted light measuring section 13 can be configured such that the cell 8 is irradiated with a light from, for example, a halogen lamp light source, and a transmitted light is dispersed by a diffraction grating, and then, a dispersed light is received by a photodiode array. The wavelengths of the light to be received are 340 nm, 405 nm, 450 nm, 480 nm, 505 nm, 546 nm, 570 nm, 600 nm, 660 nm, 700 nm, 750 nm, and 800 nm. The data on the amount of the transmitted light entering these light receivers is sent to the data storage section in the PC through the transmitted light measuring circuit.

Figure 6:
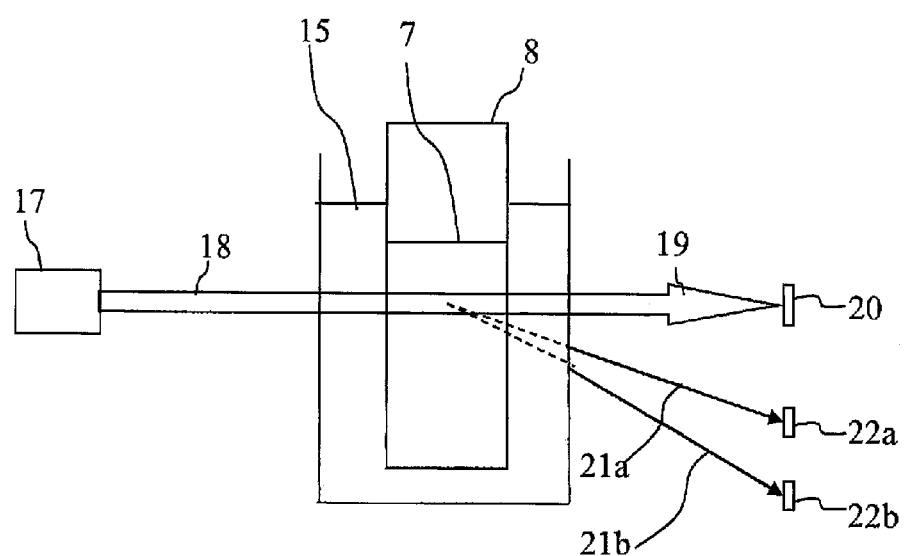
FIG. 6 is a schematic view of a scattered light measuring section.

A schematic view of the scattered light measuring section 16 is shown in FIG. 6. As the light source, for example, an LED light source or the like can be used. The cell 8 in motion is irradiated with an irradiation light 18 from an LED light source unit 17 shown in this drawing, and a transmitted light 19 is received by a transmitted light receiver 20 in the scattered light measuring section. In the LED light source unit 17, as the wavelength of the irradiation light, for example, 700 nm can be used. In this embodiment, as the light source, an LED is used, but a laser, a xenon lamp, or a halogen lamp may be used. Scattered lights 21a and 21b forward in the direction separated at an angle of 20° or 30° with respect to the optical axis in the air are measured by scattered light receivers 22a and 22b, respectively. These scattered light receivers are arranged in a plane substantially perpendicular to the moving direction of the cell by the rotation of the cell disk. Here, as the reference position of the angle, the center of the length of a light path in the cell was defined as the origin. It is sufficient to provide as a unit which receives a scattered light from the reaction mixture, a light receiver which receives a light at a different scattering angle.

Photodiodes are disposed as the light receivers at the respective angles, however, a configuration in which a single linear array having a plurality of light receivers therein is disposed to receive scattered lights at a plurality of angles may be adopted. According to this, the choice of the light-receiving angles can be expanded. Further, it is also possible to dispose an optical system such as a fiber or a lens in place of the receiver to guide a light to the scattered light receiver disposed at another place.

The quantitative determination of the concentration of an analyte present in the sample 1 is performed according to the following procedure. First, a given amount of the sample 1 in the sample cup 2 is dispensed to the cell 8 by the sample dispensing mechanism 10. Subsequently, a given amount of the reagent 4 in the reagent bottle 5 is dispensed to the cell 8 by the reagent dispensing mechanism 11. When dispensing these liquids, the sample disk 3, the reagent disk 6, and the cell disk 9 are rotationally driven by the respective driving sections under the control of the control circuit to move the sample cup 2, the reagent bottle 5, and the cell 8 in accordance with the timing of the dispensing mechanisms. Subsequently, the sample 1 and the reagent 4 in the cell 8 are stirred by the stirring section 12 to form a reaction mixture 7. A transmitted light and a scattered light from the reaction mixture 7 are measured every time the cell 8 passes by the measurement positions by the transmitted light measuring section 13 and the scattered light measuring section 16 during the rotation of the cell disk 9, and the measurement data is stored as the reaction process data in the data storage section sequentially through the transmitted light measuring circuit and the scattered light measuring circuit. After the measurement is performed for a given time, for example, about 10 minutes, the inside of the cell 8 is washed by the washing mechanism 14, and an analysis is performed for the subsequent test item. In the meantime, if necessary, another reagent 4 is additionally dispensed to the cell 8 by the reagent dispensing mechanism 11, stirring is performed by the stirring section 12, and measurement is further performed for a given time. By doing this, the reaction process data on the reaction mixture 7 collected at a given time interval is stored in the data storage section. From the stored reaction process data with respect to each light-receiving angle of the scattered light measuring section, a change in light amount due to the reaction for a given time is obtained by the analysis section, and a quantitative determination result is calculated on the basis of calibration curve data retained beforehand in the data storage section and displayed by the output section. Data necessary for the control of the respective sections and the analysis is input in the data storage section from the input section. Various types of data and results stored in the storage section and an alarm are output by the output section in the form of display, etc.

FIG. 7 shows one example of a user setting screen before measurement according to the first embodiment. A user designates a test item name for the sample in the sample disk designated by the sample number and the sample position. The user selects whether the priority is given to high sensitivity or a dynamic range as the quantitative determination method beforehand. By doing this, the light-receiving angle of the reaction process data to be used when performing quantitative determination is selected. Here, an example in which the setting is made such that quantitative determination is performed by using the reaction process data on the light-receiving angle of 30° in the case where the priority is given to high sensitivity, and quantitative determination is performed by using the reaction process data on the light-receiving angle of 20° which is smaller than 30° in the case where the priority is given to a dynamic range will be described. Then, on the basis of the choice made by the user that the priority is given to high sensitivity, the setting is made such that a quantitative determination result is output using the reaction process data on the light-receiving angle of 30°.

The light-receiving angle designated for the reaction process data to be used when performing quantitative determination may be input by a user beforehand on the basis of a parameter recommended by the manufacturer of the reagent with respect to each reagent. Further, a case where a user designates and inputs the light-receiving angle for acquiring the reaction process data to be used for quantitative determination is described here, but it may be automatically set beforehand on the device side.

Figure 8:
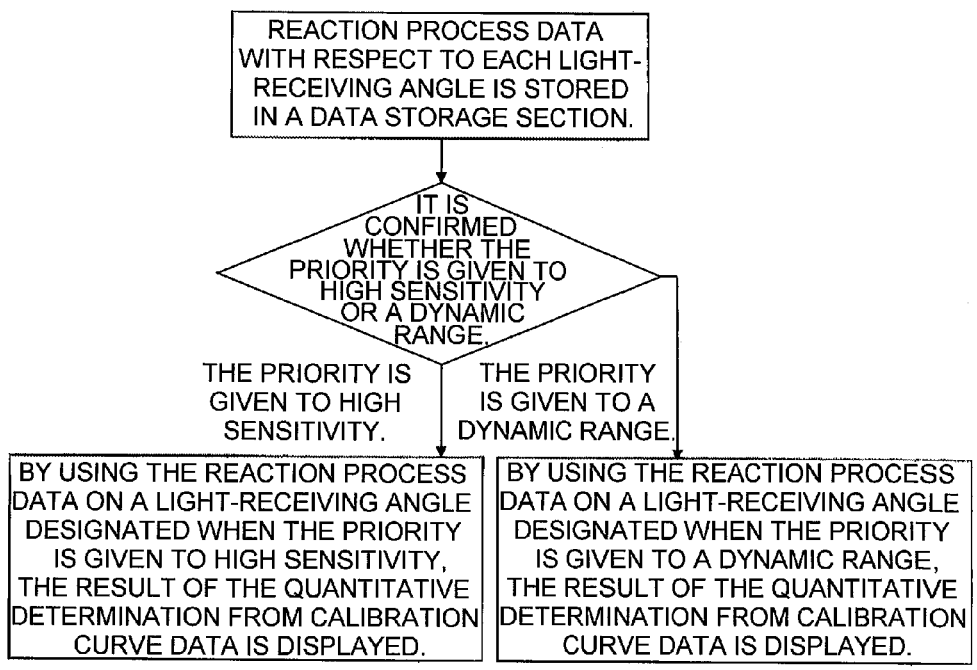
FIG. 8 is a flowchart of a first embodiment.

FIG. 8 shows a flow of a procedure until a quantitative determination result after measurement is displayed according to the first embodiment. After completion of the measurement, the reaction process data with respect to each light-receiving angle in the data storage section is collected and stored in the data storage section. Subsequently, it is confirmed whether the priority is given to high sensitivity or a dynamic range in the above-described user setting screen. Here, the priority is given to high sensitivity, and therefore, by using the reaction process data on the light-receiving angle of 20°, which has been set, quantitative determination is performed with calibration data on the designated light-receiving angle stored in the data storage section, and the result is displayed.

Figure 1:
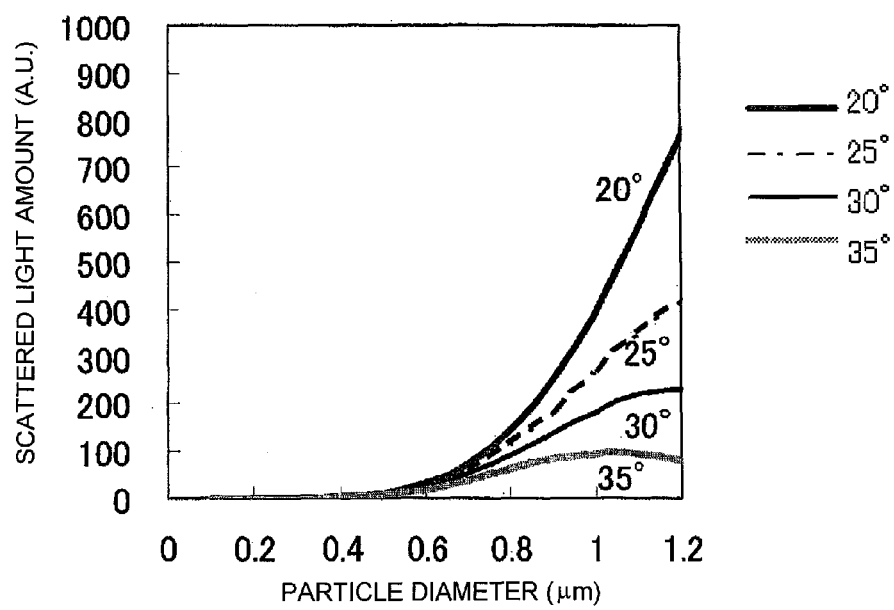
FIG. 1 is a view showing the particle diameter dependence (particle diameter: up to 1.2 µm) of a scattered light amount with respect to each light-receiving angle.

In order to compare the dynamic range with respect to each light-receiving angle in the measurement of a scattered light, the particle diameter dependence of the amount of a scattered light generated when a single polystyrene particle (refractive index: 1.59) present in water is irradiated with a light with a wavelength of 600 to 800 nm with respect to each light-receiving angle is shown in FIG. 1. The amount of a scattered light from a reaction mixture can be easily inferred from the amount of a scattered light from a single particle. The light-receiving angle is an angle formed by the optical axis of an irradiation light and the optical axis of a received light, and was set to 20°, 25°, 30°, and 35° with respect to the optical axis of an irradiation light in the air. Further, the angular resolution was set to 2.5°. That is, in the case where the light-receiving angle was 20°, in fact, an average light amount of a scattered light at a light-receiving angle ranging from 17.5° to 22.5° was calculated. The calculation was performed using Mie scattering theory. The Mie scattering theory is described in, for example, the following Non Patent Literature.

Non Patent Literature

C. F. Bohren, D. R. Huffman, Absorption and Scattering of Light by Small Particles, J. Wiley & Sons, 1983

Latex particles contained in the reagent of the automatic analysis device are considered to have a size ranging from 0.1 μm to 0.4 μm. In a latex immunoassay, it is considered that as the concentration of an analyte contained in a sample is higher, that is, as the concentration range is higher, the size of an agglutinated body (a scattering body) contained in a reaction mixture after the lapse of a predetermined time is increased, and the size of the agglutinated body is increased to 0.8 μm or more. Therefore, a light-receiving angle at which a change in particle diameter which is 0.8 μm or more can be measured is regarded as a light-receiving angle with a wide measurement range including a high concentration range. In FIG. 1, the increment of the scattered light amount at a light-receiving angle of 35° is small in the case where the particle diameter is 0.8 μm or more, however, the scattered light amount at a light-receiving angle of 20° is increased in the case where the particle diameter is 0.8 μm or more, up to at least 1.2 μm. Therefore, it is found that there is a tendency that the scattered light amount is increased as the light-receiving angle is smaller even if the particle diameter is increased, and the measurement range is wide including a high concentration range. In particular, in the case of the measurement for an agglutination reaction to form an agglutinated body with a particle diameter of 0.8 μm or more, it is found that the measurement at a light-receiving angle of 20° or 25° is more advantageous than the measurement at a light-receiving angle of 30° or 35°. In this manner, it becomes possible to perform measurement with an expanded dynamic range by using the reaction process data obtained by measurement at a smaller light-receiving angle for quantitative determination.

Figure 2:
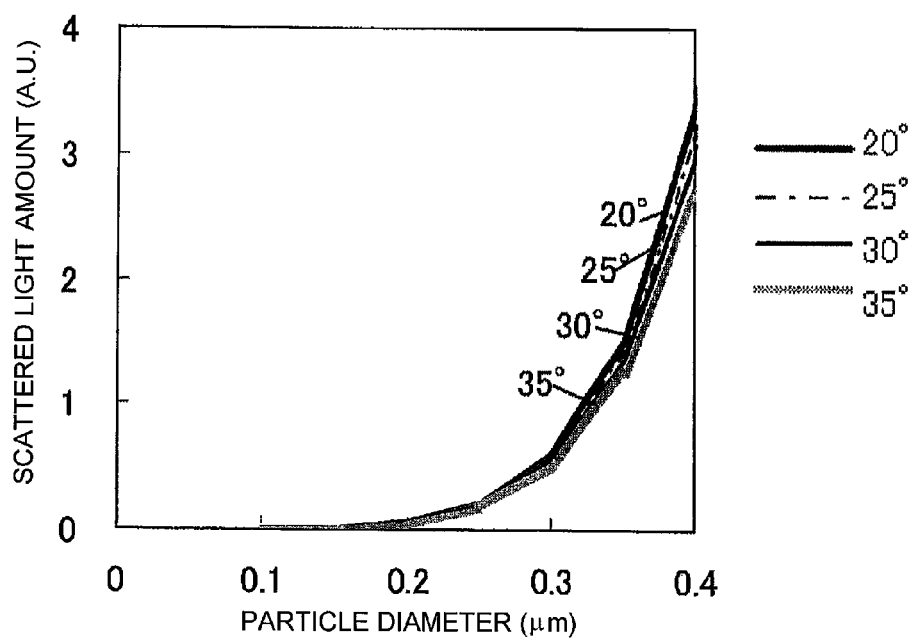
FIG. 2 is a view showing the particle diameter dependence (particle diameter: up to 0.4 µm) of a scattered light amount with respect to each light-receiving angle.

Next, the sensitivity in a low concentration range is compared with respect to each light-receiving angle. It is considered that in a low concentration range, the particle diameter of an agglutinated body is substantially the same as that of a latex particle of the reagent. It is assumed that the particle diameter of the reagent is 0.1 μm and the particle diameter of an agglutinated body is about 0.4 μm. In FIG. 2, the particle diameter dependence of the scattered light amount when the particle diameter is from about 0.1 μm to 0.4 μm is compared with respect to each angle. From FIG. 2, it is found that even if the light-receiving angle is changed, there is no significant difference in the scattered light amount when the particle diameter is from about 0.1 μm to 0.4 μm at an angle ranging from 20° to 35°. That is, it is found that a change in light amount (signal) with respect to a change in particle diameter at a low concentration is substantially the same at any angle.

Figure 3:
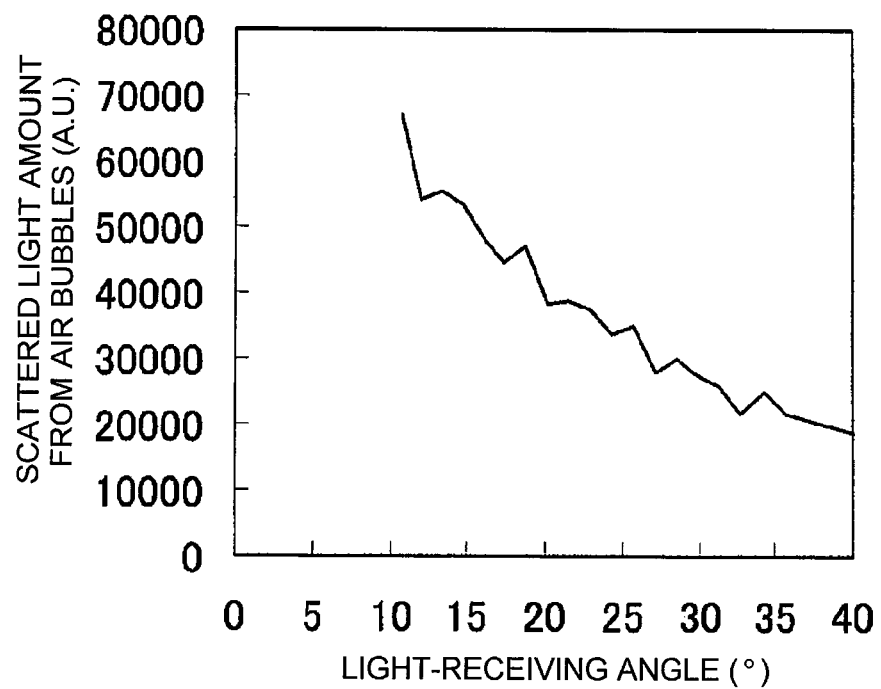
FIG. 3 is a view showing the light-receiving angle dependence of the level of an average amount of a scattered light (noise) from an air bubble.

Since a change in light amount (signal) in a low concentration range is small, it is necessary to take into consideration the noise. In order to compare the noise in a low concentration range with respect to each light-receiving angle, it is assumed that there exist air bubbles of several tens of micrometer order in a constant temperature fluid, and the angle dependence of an average scattered light amount due to air bubbles with a size of about 10 μm to 40 μm is shown in FIG. 3. From FIG. 3, it is considered that as the light-receiving angle is smaller, a scattered light from air bubbles enters more easily, and thus, the noise is larger. In order to take into consideration the ratio of the signal to the noise, the ratio of the signal when a scattered light is obtained for $10^9$ latex particles in the case where the particle diameter of the latex particle is 0.1 μm to the noise is defined as an S/N ratio, and the angle dependence of the S/N ratio is shown in FIG. 4.

Figure 4:
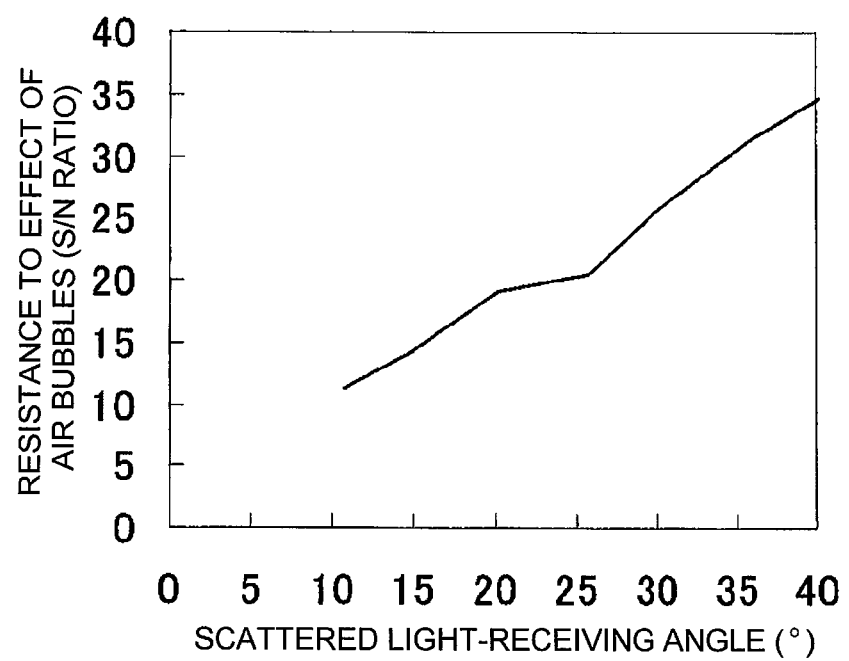
FIG. 4 is a view showing the light-receiving angle dependence of resistance to noise from an air bubble (S/N ratio).

From FIG. 4, it is indicated that the S/N ratio is larger in the case where the light-receiving angle is 35° than in the case where the light-receiving angle is 20°. From this result, it is found that as the light-receiving angle for use in a low concentration range, a relatively large angle such as 30° or 35° is advantageous to the S/N ratio, however, as the light-receiving angle for use in a high concentration range, the measurement at a small angle such as 20° or 25° is advantageous since such a small angle enables the measurement of a change in particle diameter which is large also in consideration of the results shown in FIG. 1.

From the above-described examinations, it is found that it is effective to use a relatively large angle such as 30° or 35° for quantitative determination in the case where higher sensitivity is needed, but it is effective to use a relatively small angle such as 20° or 25° for quantitative determination in the case where the priority is given to a dynamic range. It is also found that it is effective to perform quantitative determination using a relatively large light-receiving angle such as 30° or 35° in a low concentration range, but it is effective to perform quantitative determination using a relatively small light-receiving angle such as 20° or 25° in a high concentration range.

Second Embodiment

A case where light receivers are disposed at positions of 20° and 30° with respect to a light emitted from a light source as a plurality of light-receiving angles at which a scattered light is measured, and in the case where a result calculated as a change in light amount within a predetermined time period from the reaction process data is outside a measurement range defined by a lower threshold limit and an upper threshold limit, the light-receiving angle of the reaction process data to be used for calculating a quantitative value is automatically selected so as to expand a dynamic range will be described.

The basic condition is the same as that of the first embodiment, but a user setting screen before measurement and a flow of a procedure until a quantitative determination result after measurement is displayed are different from the first embodiment.

FIG. 9 shows one example of a user setting screen before measurement according to the second embodiment. A user designates a test item name for the sample in the sample disk designated by the sample number and the sample position. The user sets the light-receiving angles of the first priority and the second priority beforehand for a scattered light receiver to be used for quantitative determination. Here, the quantitative determination is basically performed at an angle designated as the first priority, however, if the result of the reaction process data at the light-receiving angle designated as the first priority shows a value outside the measurement range defined by a lower threshold limit and an upper threshold limit, a quantitative value is calculated at a second light-receiving angle, which is the subsequent light-receiving angle. These light-receiving angles which are types of the reaction process may be input by a user beforehand on the basis of a parameter recommended by the manufacturer of the reagent with respect to each reagent. Further, the light-receiving angle may be automatically set beforehand on the device side.

In this embodiment, the light-receiving angle of the first priority is set to 30° and the light-receiving angle of the second priority is set to 20°, and therefore, the light-receiving angle of the first priority is specified to be larger than the light-receiving angle of the second priority. By doing this, it becomes possible to perform a more highly sensitive measurement. In the case where the priority is given to a dynamic range, the light-receiving angle of the first priority may be set to 20° and the light-receiving angle of the second priority may be set to 30°. Further, the user does not designate these light-receiving angles, but only designates whether the priority is given to high sensitivity or a dynamic range, and when the scattered light amount in the reaction process data has reached a value exceeding the threshold, the light-receiving angle may be automatically changed. Further, in the case where the light-receiving angle is changed, when the quantitative value is displayed, the light-receiving angle used for the quantitative determination is also displayed at the same time. This enables the user to easily recognize the light-receiving angle used for obtaining the quantitative value.

Figure 10:
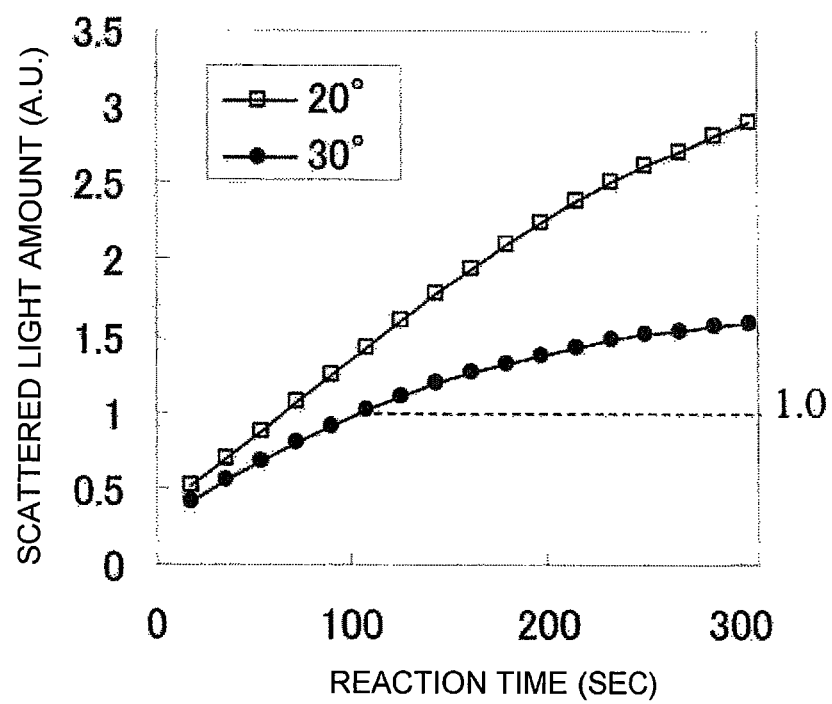
FIG. 10 shows reaction process data obtained by measurement using a CRP reagent at light-receiving angles of 20° and 30°.

Further, the upper and lower threshold limits for the respective angles are also input. Here, the thresholds are set on the basis of the scattered light amount, and when the angle is 30°, 0 is input as the lower limit and 1.0 is input as the upper limit, and when the angle is 20°, 0.8 is input as the lower limit and 10.0 is input as the upper limit. FIG. 10 shows the reaction process data obtained by measurement using a CRP reagent at light-receiving angles of 20° and 30° at a CRP of 18 mg/dL. In the case where the priority is given to high sensitivity and the angle is set to 30°, the scattered light amount (A.U.) shows linearity up to about 1.0, but when the scattered light amount is 1.0 or more, the reaction curve is blunted. Therefore, the upper threshold limit at a light-receiving angle of 30° was set to 1.0, and in the case where the scattered light amount reached a value exceeding 1.0, the light-receiving angle was changed to the second priority angle set to a smaller angle, and the quantitative determination was performed. Further, also for the light-receiving angle of the second priority, a quantitatively determinable range was determined beforehand, and the lower threshold limit was set to 0.8, and the upper threshold limit was set to 10.0.

Figure 11:
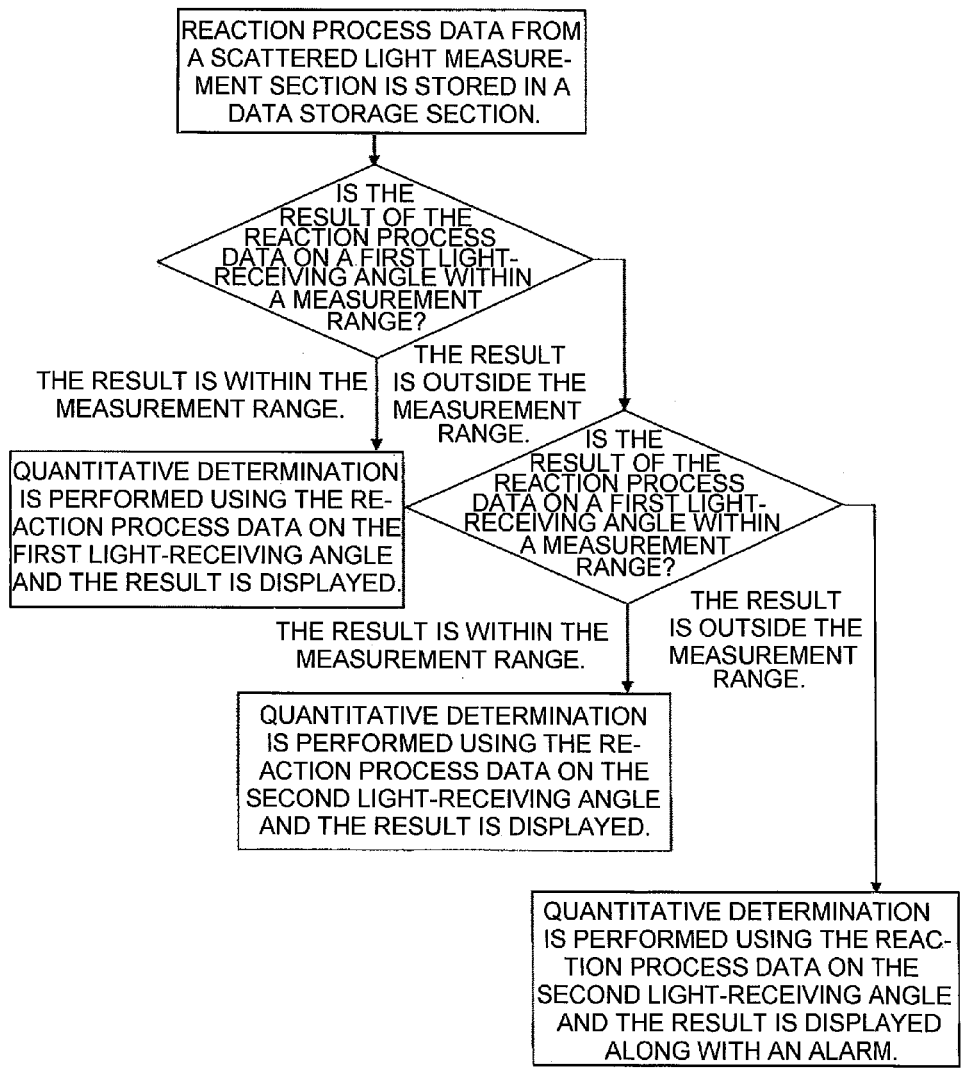
FIG. 11 is a flowchart of a second embodiment.

A flow of a procedure until a quantitative determination result after measurement is displayed according to the second embodiment is shown in FIG. 11. The reaction process data in accordance with each light receiver from the scattered light measuring section is stored in the data storage section. Then, it is confirmed whether the result of the reaction process data on the first light-receiving angle (a change in light amount within a predetermined time period) is within or outside a measurement range defined by an upper or lower threshold limit. Here, in the case where the result is within the measurement range, quantitative determination is performed using the reaction process data on the light-receiving angle of the first priority, and the result is displayed. In the case where the result is outside the measurement range, it is confirmed whether the reaction process data on the light-receiving angle of the second priority is within or outside a measurement range defined by an upper or lower threshold limit. In the case where the data is within the measurement range, quantitative determination is performed using the reaction process data on the light-receiving angle of the second priority, and the result is displayed. In the case where the data is outside the measurement range, the result of the quantitative determination obtained using the reaction process data on the light-receiving angle of the second priority and an alarm which indicates that the result exceeds the threshold are displayed at the same time.

Incidentally, here, a case where the number of the scattered light receivers is 2 is described, however, it is also possible to set the priority order to third or lower in the case where the number of the light receivers is 3 or more.

Third Embodiment

A case where quantitative determination is performed using each reaction process data on the designated light-receiving angle, and when a difference between the thus obtained quantitative values is a predetermined value or more, the result at the light-receiving angle designated to be preferentially displayed with the quantitative value is displayed will be described.

The basic condition is the same as that of the second embodiment, but a user setting screen before measurement and a flow of a procedure until a quantitative determination result after measurement is displayed are different from the second embodiment.

FIG. 12 shows one example of a user setting screen before measurement according to the third embodiment. It is basically the same as that of the second embodiment, but it is configured such that a quantitative alarm value to be used in checking whether an alarm is displayed or not can be set.

The respective quantitative values calculated from the reaction process data on the light-receiving angles designated in the setting screen are compared, and when a difference between the quantitative values exceeds the quantitative alarm value, an alarm may be displayed. Further, in this embodiment, the quantitative alarm value is compared with the difference between the quantitative values, but may be a percentage (%) indicating what percentage the quantitative value deviates. One example of a screen in which the quantitative determination result after measurement is displayed according to the third embodiment is shown in FIG. 13. Here, the quantitative determination result using the reaction process data on the light-receiving angle of 30° is 0.5 mg/dL, the quantitative determination result using the reaction process data on the light-receiving angle of 20° is 0.8 mg/dL, and a difference between these quantitative values is 0.1 mg/dL or more, and based on these results, 0.5 mg/dL which is the quantitative value obtained from the reaction process data on the light-receiving angle of 30° designated as the first priority is displayed as the quantitative value.

Here, a case where the number of the light-receiving angles is 2 is described, however, also in the case where the number of the light-receiving angles is 3 or more, it is possible to set an angle to be preferentially output on the basis of a difference or a deviation percentage between the quantitative values. Further, an alarm is displayed along with the quantitative determination result. This can urge the user to confirm the detailed quantitative determination result. Further, by displaying the quantitative value with respect to each of the designated light-receiving angles in a list as shown in the drawing, it becomes easy for the user to confirm the values.

Incidentally, in the first to third embodiments, an example in which the designation of the light-receiving angle is made one by one according to the purpose is described, however, a configuration in which light receivers at a plurality of light-receiving angles are selected by designating an angle range may be adopted. Further, in the case where there is a light-receiving angle at which the quantitative determination result exceeds the upper or lower threshold limit as in the second embodiment in the designated angle range, quantitative determination may be performed using the reaction process data obtained by measurement using a light receiver at a light-receiving angle at which the quantitative determination result does not exceed the threshold.

Further, in this embodiment, the device is applied to a latex immunoassay, but may be applied to an immunoassay which does not use a latex as a sensitizer.

REFERENCE SINGS LIST

1 Sample
2 Sample cup
3 Sample disk
4 Reagent
5 Reagent bottle
6 Reagent disk
7 Reaction mixture
8 Cell
9 Cell disk
10 Sample dispensing mechanism
11 Reagent dispensing mechanism
12 Stirring section
13 Transmitted light measuring section
14 Washing section
15 Constant temperature fluid
16 Scattered light measuring section
17 LED light source unit
18 Irradiation light
19 Transmitted light
20 Transmitted light receiver
21a, 21b Scattered light
22a, 22b Scattered light receiver
23 Control circuit
24 Transmitted light measuring circuit
25 Scattered light measuring circuit
26 Data processing section
27 Input section
28 Output section

The invention claimed is:

1. An automatic analysis device comprising:
a cell in which a reaction mixture obtained by mixing a sample with a reagent is placed;
a rotatable cell disk which holds the cell on a circumference thereof;
a light source which irradiates the cell with a light;
a plurality of light receivers which receive, at different respective light-receiving angles, scattered light that is scattered due to the reaction mixture placed in the cell, the different respective light-receiving angles including a larger light-receiving angle and a smaller light-receiving angle;
a data processing section which processes reaction process data on the reaction mixture obtained using the plurality of light receivers, the reaction process data including information on the scattered light received at the different respective light receiving angles; and
an output section which outputs a result of processing by the data processing section, wherein:
the data processing section stores information on the respective light-receiving angles, and
the data processing section is configured to select, based on the information on the respective light-receiving angles, the reaction process data to be used for determining a quantitative value of the reaction mixture from the reaction process data obtained using the plurality of light receivers, wherein:
the larger light-receiving angle is selected and used for measuring a smaller value for the quantitative value, which corresponds to a lower concentration to be measured for the reaction mixture, and
the smaller light-receiving angle is selected and used for measuring a larger value for the quantitative value, which corresponds to a higher concentration to be measured for the reaction mixture, and
the data processing section is configured to determine and output, as the result, the quantitative value of the reaction mixture based on the selected reaction process data,
wherein the information on the respective light-receiving angles further comprises:
information on a threshold difference corresponding to a difference between multiple quantitative values determined using the reaction process data obtained using the plurality of light receivers, and
information on a particular light-receiving angle to use when the difference between the multiple quantitative values exceeds the threshold difference,
wherein, when the difference between the multiple quantitative values exceeds the threshold difference, the reaction process data selected to be used for determining the quantitative value of the reaction mixture is selected at least partially based on the information on the particular light-receiving angle.

2. The automatic analysis device according to claim 1, wherein the information on the respective light-receiving angles further comprises information on the respective light-receiving angles in accordance with respective quantitative values for the reaction mixture.

3. The automatic analysis device according to claim 1, further comprising an input section which is configured to input at least a portion of the information on the respective light-receiving angles of the plurality of light receivers.

4. The automatic analysis device according to claim 1, wherein the cell is configured to receive, as the reaction mixture, a reaction mixture in which an agglutination reaction is performed using latex particles.

5. The automatic analysis device according to claim 1, wherein:
the light source is configured to irradiate the cell with a wavelength of light from about 600 to 800 nm, and
the data processing section is configured to determine the quantitative value using the reaction process data on a light-receiving angle of 17.5° to 27.5° among the respective light-receiving angles of the plurality of light receivers when a size of a scattering body contained in the reaction mixture is 0.8 µm or more.

6. An automatic analysis device comprising:
a cell in which a reaction mixture obtained by mixing a sample with a reagent is placed;
a rotatable cell disk which holds the cell on a circumference thereof;
a light source which irradiates the cell with a light;
a plurality of light receivers which receive, at different respective light-receiving angles, scattered light that is scattered due to the reaction mixture placed in the cell, the different respective light-receiving angles including a larger light-receiving angle and a smaller light-receiving angle;
a data processing section which processes reaction process data on the reaction mixture obtained using the plurality of light receivers, the reaction process data including information on the scattered light received at the different respective light receiving angles; and
an output section which outputs a result of processing by the data processing section, wherein:

the data processing section stores information on the respective light-receiving angles, and the data processing section is configured to select, based on the information on the respective light-receiving angles, the reaction process data to be used for determining a quantitative value of the reaction mixture from the reaction process data obtained using the plurality of light receivers, wherein:

the larger light-receiving angle is selected and used for measuring a smaller value for the quantitative value, which corresponds to a lower concentration to be measured for the reaction mixture, and the smaller light-receiving angle is selected and used for measuring a larger value for the quantitative value, which corresponds to a higher concentration to be measured for the reaction mixture, and the data processing section is configured to determine and output, as the result, the quantitative value of the reaction mixture based on the selected reaction process data, wherein the information on the respective light-receiving angles further comprises:

information on a threshold deviation percentage corresponding to a deviation percentage between multiple quantitative values determined using the reaction process data obtained using the plurality of light receivers, and information on a particular light-receiving angle to use when the deviation percentage between the multiple quantitative values exceeds the threshold deviation, wherein, when the deviation percentage between the multiple quantitative values exceeds the threshold deviation, the reaction process data selected to be used for determining the quantitative value of the reaction mixture is selected at least partially based on the information on the particular light-receiving angle.

7. An automatic analysis device comprising:

a cell in which a reaction mixture obtained by mixing a sample with a reagent is placed;

a rotatable cell disk which holds the cell on a circumference thereof;

a light source which irradiates the cell with a light;

a plurality of light receivers which receive, at different respective light-receiving angles, scattered light that is scattered due to the reaction mixture placed in the cell, the different respective light-receiving angles including a larger light-receiving angle and a smaller light-receiving angle;

a data processing section which processes reaction process data on the reaction mixture obtained using the plurality of light receivers, the reaction process data including information on the scattered light received at the different respective light receiving angles; and an output section which outputs a result of processing by the data processing section, wherein:

the data processing section stores information on the respective light-receiving angles, and the data processing section is configured to select, based on the information on the respective light-receiving angles, the reaction process data to be used for determining a quantitative value of the reaction mixture from the reaction process data obtained using the plurality of light receivers, wherein:

the larger light-receiving angle is selected and used for measuring a smaller value for the quantitative value, which corresponds to a lower concentration to be measured for the reaction mixture, and the smaller light-receiving angle is selected and used for measuring a larger value for the quantitative value, which corresponds to a higher concentration to be measured for the reaction mixture, and the data processing section is configured to determine and output, as the result, the quantitative value of the reaction mixture based on the selected reaction process data, wherein the information on the respective light-receiving angles further comprises:

information on a first light-receiving angle that is used for outputting the quantitative value of the reaction mixture, information on a first threshold of the reaction process data on the first light-receiving angle, and information on a second light-receiving angle that is used for outputting the quantitative value of the reaction mixture when the reaction process data on the first light-receiving angle is outside the first threshold.

8. The automatic analysis device according to claim 7, wherein:

the data processing section further stores information on a second threshold of the reaction process data on the second light-receiving angle, and when the reaction process data on the second light-receiving angle is outside the second threshold, the data processing section is configured to provide to the output section, as the result, an alarm and the quantitative value, wherein the quantitative value is determined based on the reaction process data on the second light-receiving angle.

* * * * *